United States Patent
Lange de Oliveira et al.

(10) Patent No.: US 10,538,478 B2
(45) Date of Patent: Jan. 21, 2020

(54) CATALYST MODIFICATION WITH ALKALI METAL, ALKALINE EARTH METAL OR RARE EARTH METAL IONS IN THE CONTINUOUS LIQUID-PHASE HYDROGENATION OF NITRO COMPOUNDS

(71) Applicant: BASF SE, Ludwigshafen am Rhein (DE)

(72) Inventors: Armin Lange de Oliveira, Heidelberg (DE); Barbara Wucher, Ludwigshafen (DE); Christian Bechtold, Ludwigshafen (DE); Michael Friko, Ludwigshafen (DE); Renate Hempel, Ruhland (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/340,593

(22) PCT Filed: Oct. 10, 2017

(86) PCT No.: PCT/EP2017/075746
§ 371 (c)(1),
(2) Date: Apr. 9, 2019

(87) PCT Pub. No.: WO2018/069278
PCT Pub. Date: Apr. 19, 2018

(65) Prior Publication Data
US 2019/0233364 A1 Aug. 1, 2019

(30) Foreign Application Priority Data

Oct. 10, 2016 (EP) .................................... 16193137

(51) Int. Cl.
*C07C 209/36* (2006.01)
*B01J 23/89* (2006.01)
*C07C 211/50* (2006.01)
*C07C 209/82* (2006.01)

(52) U.S. Cl.
CPC ............ *C07C 209/36* (2013.01); *B01J 23/892* (2013.01); *C07C 211/50* (2013.01); *B01J 2523/828* (2013.01); *B01J 2523/847* (2013.01); *C07C 209/82* (2013.01)

(58) Field of Classification Search
None
See application file for complete search history.

(56) References Cited

U.S. PATENT DOCUMENTS

| | | | |
|---|---|---|---|
| 6,140,539 A | 10/2000 | Sander et al. |
| 6,350,911 B1 | 2/2002 | Sander et al. |
| 6,677,271 B1 | 1/2004 | Birke et al. |
| 6,680,280 B1 | 1/2004 | Birke et al. |
| 2005/0177003 A1 | 8/2005 | Vanoppen et al. |
| 2005/0215567 A1 | 9/2005 | Bakker et al. |
| 2006/0014761 A1 | 1/2006 | Morgan et al. |
| 2008/0177111 A1 | 7/2008 | Van Laar et al. |
| 2008/0242537 A1 | 10/2008 | Kubanek et al. |
| 2009/0036447 A1 | 2/2009 | Morgan et al. |
| 2009/0099198 A1 | 4/2009 | Morgan et al. |
| 2010/0130788 A1 | 5/2010 | Coelho Tsou et al. |
| 2011/0275858 A1 | 11/2011 | Coelho Tsou et al. |
| 2012/0071316 A1 | 3/2012 | Voss et al. |
| 2012/0172372 A1 | 7/2012 | Morgan et al. |
| 2013/0190500 A1 | 7/2013 | Greiner et al. |
| 2014/0038983 A1 | 2/2014 | Morgan et al. |
| 2014/0039227 A1 | 2/2014 | Neto et al. |
| 2015/0005296 A1 | 1/2015 | Morgan et al. |
| 2015/0050239 A1 | 2/2015 | Xi et al. |
| 2016/0115133 A1 | 4/2016 | Morgan et al. |
| 2017/0267638 A1 | 9/2017 | Morgan et al. |

FOREIGN PATENT DOCUMENTS

| | | |
|---|---|---|
| CN | 104402731 A | 3/2015 |
| DE | 10 2005 041 532 A1 | 3/2007 |
| DE | 10 2008 063 308 B4 | 3/2013 |
| EP | 1 161 297 | 12/2001 |

(Continued)

OTHER PUBLICATIONS

International Search Report dated Jan. 3, 2018 in PCT/EP2017/075746, citing documents AA, AB, AO, AP, AW-AY therein, 4 pages.
International Preliminary Report on Patentability and Written Opinion dated Apr. 11, 2019 in PCT/EP2017/075746, citing documents AA, AB, AO, AP, AW-AY therein, 8 pages.
M.M. Telkar et al., "Role of a Co-metal in Bimetallic Ni—Pt Catalyst for Hydrogenation of m-dinitrobenzene to m-phenylenediamine", Applied Catalysis A: General, Elsevier, vol. 295, No. 1, XP027814501, Oct. 13, 2005, pp. 23-30.
Zhengkun Yu et al., "Hydrogenation of Nitroaromatics by Polymer-anchored Bimetallic Palladium-ruthenium and Palladium-platinum Catalysts Under Mild Conditions", Journal of Molecular Catalysis A: Chemical., vol. 120, No. 1-3, XP055356085, Jun. 1, 1997, pp. 247-255.

(Continued)

*Primary Examiner* — Ana Z Muresan
(74) *Attorney, Agent, or Firm* — Oblon, McClelland, Maier & Neustadt, L.L.P.

(57) ABSTRACT

The present invention relates to a process for continuous hydrogenation of a nitro compound to the corresponding amine in a liquid reaction mixture comprising the nitro compound in the presence of a supported catalyst which comprises as the active component at least one element from groups 7 to 12 of the periodic table of the elements, wherein the hydrogenation is performed in the presence of at least one salt selected from the group consisting of the salts of the alkali metals, alkaline earth metals and of the rare earth metals and to a supported catalyst for continuous hydrogenation of a nitro compound to the corresponding amine in a liquid reaction mixture comprising the nitro compound which comprises as the active component at least one element from groups 7 to 12 of the periodic table of the elements and one salt of the alkali metals, alkaline earth metals or of the rare earth metals.

16 Claims, 5 Drawing Sheets

(56) References Cited

FOREIGN PATENT DOCUMENTS

| | | |
|---|---|---|
| EP | 1 165 231 | 1/2002 |
| EP | 1 678 118 | 7/2006 |
| WO | WO 00/35852 A1 | 6/2000 |
| WO | WO 00/51727 A1 | 9/2000 |
| WO | WO 00/51728 A1 | 9/2000 |
| WO | WO 03/066571 A1 | 8/2003 |
| WO | WO 2005/037768 A1 | 4/2005 |
| WO | WO 2005/092340 A1 | 10/2005 |
| WO | WO 2008/138784 A1 | 11/2008 |
| WO | WO 2008/145179 A1 | 12/2008 |
| WO | WO 2010/125025 A1 | 11/2010 |
| WO | WO 2014/022116 A2 | 2/2014 |
| WO | WO 2014/108351 A1 | 7/2014 |

OTHER PUBLICATIONS

Rasika B. Mane et al., "Selectivity Tuning Options in Hadrogenation of m-Chloronitrobenzene to m-Chloroaniline over Mono- and Bimetallic Supported Catalysts", Industrial And Engineering Chemistry Research, vol. 51, XP002768353, 2012, pp. 15564-15572.

CATALYST MODIFICATION WITH ALKALI METAL, ALKALINE EARTH METAL OR RARE EARTH METAL IONS IN THE CONTINUOUS LIQUID-PHASE HYDROGENATION OF NITRO COMPOUNDS

The present invention relates to a process for continuous hydrogenation of a nitro compound to the corresponding amine in a liquid reaction mixture comprising the nitro compound in the presence of a supported catalyst which comprises as the active component at least one element from groups 7 to 12 of the periodic table of the elements, wherein the hydrogenation is performed in the presence of at least one salt of the alkali metals, alkaline earth metals or of the rare earth metals.

Processes for continuous hydrogenation of nitro compounds to the corresponding amines are known per se.

CN 104402731 A describes a process for producing aniline compounds by catalytic hydrogenation of mononitrobenzene compounds. The reaction is performed in a discontinuous process at a temperature of 20° C. to 80° C. 1 to 10 mol % of metal salts are supplied to the reaction based on the total amount of the substrate. A disadvantage of the process described in CN 104402731 A is that it is performed discontinuously which results in unnecessary reactor downtime, increased catalyst consumption and marked quality variations between the different batches. A further disadvantage is that large amounts of metal salts need to be supplied which results in increased production costs. The salts used (halides) moreover promote metal corrosion.

Furthermore, a commonly described difficulty in processes for hydrogenation of nitro compounds to the corresponding amines is the release of large amounts of reaction heat and associated potentially high reaction temperatures.

DE 10 2008 063308 B4 describes a process for producing tolylenediamine by hydrogenation of dinitrotoluene where the reaction heat is utilized for obtaining steam which is introduced into a steam network of an industrial plant and may be utilized further. Steam generation necessarily requires reaction temperatures greater than 100° C. The hydrogenation disclosed in DE 10 2008 063308 B4 is performed at a temperature of not less than 180° C.

However, an often described problem of high reaction temperatures during hydrogenation are undesired side reactions which also proceed via local hotspots inside the reactor for example.

WO 2014/108351 A1 describes an apparatus of the loop venturi reactor type for the continuous reaction of liquids with gases, in particular for hydrogenations, oxidations or acetylations, for example for the production of tolylenediamine by hydrogenation of dinitrotoluene. In the case of a large amount of evolved reaction heat local temperature spikes are avoided by modification of the arrangement of the heat transfer tubes of the reactor. Catalysts used are for example activated nickel catalysts according to WO 2008/145179 A1 which are composed of a doped Ni/Al alloy and are not supported. One problem with such Ni/Al alloys is the formation of nickel aluminates, such as takovite or takovite-like compounds. Nickel aluminates are formed in the hydrogenation of nitroaromatics when the Ni/Al catalyst comprises more than 5.5 wt % of Al. They form solids which are deposited on the walls of the reactor and the peripheral apparatuses, such as pumps. This can result in a reduction in the efficiency of heat transfer of the system and even in blockages of the system. One or more metals selected from the group consisting of Mg, Ce, Ti, V, Nb, Cr, W, Mn, Re, Fe, Ru, Co, Rh, Ir, Pt, Cu, Ag, Au and Bi are used to dope the Ni/Al alloy of the activated nickel catalyst from WO 2008/145179 A1 in order to reduce or completely avoid the formation of nickel aluminates such as takovite or takovite-like compounds.

WO 00/35852 discloses a process for producing amines by catalytic hydrogenation of nitro compounds. The problem of increased occurrence of undesired side reactions is countered by optimization of the construction and mode of operation of the reactor used which are intended to avoid the local hotspots that bring about the side reactions.

EP 1678118 B1 discloses a process for producing amines by catalytic hydrogenation of the corresponding nitro compounds. In order to combat side reactions which result in the formation of high molecular weight byproducts or in the formation of low boilers the selectivity of the process is improved using a catalyst consisting of platinum and nickel.

DE 10 2005 041532 A1 likewise describes a process for producing amines by catalytic hydrogenation of the corresponding nitro compounds with reduced side reactions and improved selectivity of the process using a catalyst consisting of platinum, nickel and an additional metal.

A further problem with the known processes is that after a prolonged running time of the reaction process, the product yield is reduced on account of the aging of the catalyst. For example impurities in the reactant supplied, or the products of undesired side reactions, can contribute to the aging of the catalyst. The aging of the catalyst may additionally be accelerated by an interruption in the supply of the reactant, for example during a pause in operation.

When a reactor with recycling of matter, a so-called loop reactor, is employed there may be regions in which a complete conversion of the reactant takes place. The aging of the catalyst may be accelerated in these regions since as a result of the complete conversion of the reactant the formation of high-boiling components, such as various amino- and methyl-substituted diphenylamines, hydrazodiphenyls and phenazines, takes place to a greater extent.

Furthermore, an interruption in the supply of nitro compounds while maintaining the reaction conditions (such as temperature, pressure, hydrogen stream and flow in the Loop reactor (circulation stream)) and all other conditions results in formation of high-boiling components, such as various amino- and methyl-substituted diphenylamines, hydrazodiphenyls and phenazines, which can deactivate the catalyst. When the process is resumed by renewed supply of nitro compounds the yield of amines is markedly lower and generally recovers only slowly and in-completely.

It is an object of the present invention in a process for continuous hydrogenation of nitro corn-pounds to the corresponding amines to maintain the activity of the catalyst for longer periods without having to reduce the feed rate of the reactants or the temperature. It is a further object of the present invention to reduce the formation of high-boiling components which result in contamination of the catalyst and in deactivation thereof.

The object is achieved by a process for continuous hydrogenation of a nitro compound to the corresponding amine in a liquid reaction mixture comprising the nitro compound in the presence of a supported catalyst which comprises as the active component at least one element from groups 7 to 12 of the periodic table of the elements, wherein the hydrogenation is performed in the presence of at least one salt of the alkali metals, alkaline earth metals or of the rare earth metals.

The object is likewise achieved by a supported catalyst for continuous hydrogenation of a nitro compound to the corresponding amine in a liquid reaction mixture comprising the nitro compound which comprises as the active component at least one element from groups 7 to 12 of the periodic table of the elements, wherein said catalyst comprises at least one salt of the alkali metals, alkaline earth metals or of the rare earth metals.

It was found that, surprisingly, the hydrogenation in the presence of at least one salt of the alkali metals, alkaline earth metals or of the rare earth metals significantly increases the product yield of amines. Simultaneously, the formation of high-boiling components during the process is reduced and the lifetime of the catalyst increased.

Surprisingly, the formation of high-boiling components is also reduced when salts of the alkali, alkaline earth or of the rare earth metals or mixtures thereof are present in the reactor prior to an interruption in the supply of nitro compounds. The reaction yield of amines returns to its previous level immediately after resumption of the reaction through supply of nitro compounds.

The active component of the catalyst generally comprises at least one element from the group consisting of nickel, platinum, palladium, iron and cobalt.

In a first preferred embodiment the active component of the supported catalyst comprises nickel in the form of nickel crystallites having a bimodal nickel crystallite size distribution and has a nickel content of 60 to 80 wt % based on the total mass of the catalyst and a degree of reduction of at least 70%.

In a second preferred embodiment the active component of the supported catalyst comprises a mixture of nickel and platinum and optionally at least one additional metal. The hydrogenation catalyst of this second preferred embodiment preferably comprises 1 to 5 wt % of platinum, 0.3 to 1.5 wt % of nickel, 0.05 to 1.5 wt % of the at least one additional metal and 94.65 to 97.45 wt % of support material based on the total weight of the catalyst. The at least one additional metal is preferably chromium.

The at least one salt of the alkali metals, alkaline earth metals or of the rare earth metals may be comprised in the catalyst for example, preferably in a total concentration of 0.05 to 20 wt % based on the dry mass of the catalyst.

The at least one salt of the alkali metals, alkaline earth metals or of the rare earth metals may equally be comprised in the liquid reaction mixture, preferably in a total concentration of 0.01 to 1 mol % based on the supplied amount of nitro compound for hydrogenation.

The at least one salt of the alkali metals, alkaline earth metals or of the rare earth metals generally comprises potassium, strontium, sodium or mixtures thereof and is a carbonate, hydrogencarbonate, hydroxide, oxide, nitrate or carboxylate.

Nitro Compounds

The nitro compounds employed in the process according to the invention are organic corn-pounds having at least one nitro group.

Suitable nitro compounds are for example nitro alcohols and nitroaromatics.

Suitable nitro alcohols are for example tris(hydroxymethyl)nitromethane, 2-nitro-2-methyl-1,3-propanediol, 2-nitro-2-ethyl-1,3-propanediol, 2-nitro-1-butanol and 2-nitro-2-methyl-1-propanol and any desired mixtures of two or more of the recited nitro alcohols. These are hydrogenated to the corresponding aminoalcohols.

In a preferred embodiment the nitro compound for hydrogenation is a nitroaromatic. Suitable nitroaromatics are mononitroaromatics, dinitroaromatics and polynitroaromatics. Polynitroaromatics in the context of the invention are nitroaromatics having at least three nitro groups. Preference is given to hydrogenating mononitroaromatics or dinitroaromatics, particularly preferably dinitroaromatics.

The mononitroaromatics used generally have 6 to 18 carbon atoms. Suitable mononitroaromatics are mononitrotoluenes and the halogen derivatives thereof and also mononitrobenzenes and the halogen derivatives thereof, for example nitrobenzene, o-nitrotoluene, m-nitrotoluene, p-nitrotoluene, mononitroxylenes, such as 1,2-dimethyl-3-nitrobenzene, 1,2-dimethyl-4-nitrobenzene, 1,4-dimethyl-2-nitrobenzene, 1,3-dimethyl-2-nitrobenzene, 2,4-dimethyl-1-nitrobenzene and 1,3-dimethyl-5-nitrobenzene, mononitronaphthalenes, such as 1-nitronaphthalene and 2-nitronaphthalene, chloronitrobenzenes, such as o-chloronitrobenzene, m-chloronitrobenzene, p-chloronitrobenzene, or 1,2-dichloro-4-nitrobenzene, 1,4-dichloro-2-nitrobenzene, 2,4-dichloro-1-nitrobenzene and 1,2-dichloro-3-nitrobenzene, chloronitrotoluenes, such as 4-chloro-2-nitrotoluene, 4-chloro-3-nitrotoluene, 2-chloro-4-nitrotoluene and 2-chloro-6-nitrotoluene and nitroanilines, such as o-nitroaniline, m-nitroaniline or p-nitroaniline.

Preferred mononitroaromatics are mononitrobenzenes, halogenated mononitrobenzenes and mononitrotoluenes, particular preference being given to nitrobenzene, o-nitrotoluene, m-nitrotoluene, p-nitrotoluene, 1,2-dimethyl-3-nitrobenzene, 1,2-dimethyl-4-nitrobenzene, 1,4-dimethyl-2-nitrobenzene, 1,3-dimethyl-2-nitrobenzene, 2,4-dimethyl-1-nitrobenzene, 1,2-dichloro-4-nitrobenzene, 1,4-dichloro-2-nitrobenzene, 2,4-dichloro-1-nitrobenzene or 1,2-dichloro-3-nitrobenzene, very particular preference being given to o-nitrotoluene, m-nitrotoluene and p-nitrotoluene.

The dinitroaromatics used generally have 6 to 18 carbon atoms. Suitable dinitroaromatics are dinitrotoluenes and the halides thereof, dinitrobenzenes and the halides thereof and also dinitronaphthalenes. Compounds that may be used include for example 1,3-dinitrobenzene, 2,4-dinitrotoluene, 2,6-dinitrotoluene, dinitroxylenes, such as 2,4-dinitro-m-xylene, 3,5-dinitro-o-xylene, 4,5-dinitro-o-xylene or 4,6-dinitro-m-xylene, dinitronaphthalenes, such as 1,5-dinitronaphthalene or 1,8-dinitronaphthalene, or chloronitrobenzenes, such as 2-chloro-1,3-dinitrobenzene or 1-chloro-2,4-dinitrobenzene.

Preferred nitroaromatics are dinitrobenzenes, halogenated dinitrobenzenes, dinitronaphthalenes and dinitrotoluenes, particularly preferably m-dinitrobenzene, 1,5-dinitronaphthalene, 1,3-dinitrobenzene, 2,4-dinitrotoluene, 2,6-dinitrotoluene, 2-chloro-1,3-dinitrobenzene and 1-chloro-2,4-dinitrobenzene and very particularly preferably m-dinitrobenzene, 1,5-dinitronaphthalene, 2,4-dinitrotoluene and 2,6-dinitrotoluene.

The polynitroaromatics used generally have 6 to 18 carbon atoms. Suitable polynitroaromatics are for example 2,4,6-trinitrotoluene, polynitroxylenes, such as 2,4,6-trinitro-m-xylene or 4,5,6-trinitro-m-xylene.

Preferred polynitroaromatics are 2,4,6-trinitrotoluene, 2,4,6-trinitro-m-xylene or 4,5,6-trinitro-m-xylene, with 2,4,6-trinitrotoluene being particularly preferred.

Mixtures of the recited mononitroaromatics, dinitroaromatics and polynitroaromatics are also suitable in accordance with the invention.

It is preferable when the nitro compounds are nitroaromatics, preferably dinitroaromatics, particularly preferably dinitrobenzene, halogenated dinitrobenzenes and dinitrotoluenes and very particularly preferably dinitrotoluene.

In a very particularly preferred embodiment 2,4-dinitrotoluene or 2,6-dinitrotoluene is employed. Industrial mixtures comprising 2,4-dinitrotoluene and 2,6-dinitrotoluene are also suitable, wherein these mixtures preferably comprise up to 35 wt % of 2,6-dinitrotoluene with proportions of preferably 1 to 5 wt %, by preference 1 to 4 wt %, of vicinal dinitrotoluene and preferably 0.5 to 1.5 wt % of 2,5- and 3,5-dinitrotoluene based on the overall mixture.

Mixtures of the recited nitro alcohols and nitroaromatics are also suitable in accordance with the invention.

The recited nitro alcohols and nitroaromatics are commercially available.

The nitro alcohols and nitroaromatics used may furthermore be obtained by chemical synthesis, such as dinitrotoluenes may be obtained by nitration of toluene for example. The thus formed reaction product usually comprises not only the desired nitro compound but also numerous impurities. For example nitrating acid comprising nitric acid, sulfuric acid and nitrogen oxides may be present in this reaction product. Degradation products, such as dinitrogen monoxide, hydrocyanic acid, carbon monoxide or mixtures thereof for example, may also be present as impurities. Oxidation products, for example from undesired side reactions of the nitroaromatics, may likewise be present, for example aromatic carboxylic acids, such as nitrobenzoic acids, for example mononitrobenzoic acid, dinitrobenzoic acid or the degradation products thereof or mixtures thereof.

Further impurities may be present in the form of high boilers, such as nitrocresol, for example mononitrocresol, dinitrocresol or trinitrocresol and nitrophenol, for example dinitrophenol or trini-trophenol.

A purification of the thus obtained nitro compounds is thus generally necessary in order for them to be suitable as reactants for subsequent processes, for example the hydrogenation to the corresponding amines. Processes for the synthesis of nitro compounds and the further purification thereof are generally known to one skilled in the art or are described in US 2014/0039227 A1 for dinitrotoluene for example.

The purification is generally effected in a multistage washing process comprising at least three washing steps: a washing step for removal of the acids, a washing step in the presence of a base for removing weak acids and a neutral washing step for removing remaining alkaline substances.

The resulting washing solutions may comprise nitrocresols or nitroaromatics for example which may be removed for example by precipitation through acidification, by treatment with activated carbon, via strongly basic exchange columns, by extraction using toluene or the aromatic to be nitrated, by oxidation using nitric acid and subsequent thermal decomposition, by decomposition using hydrogen peroxide or ozone or by thermolysis of the nitroaromatics.

After removal of nitrating acid and any nitrocresols and/or nitrobenzoic acids present the purification of the nitroaromatics may also be effected in two washing steps as described for dinitrotoluene in US 2014/0039227 A1. In a first washing step comprising at least one extraction step the crude mixture may be washed with a first washing acid comprising nitric acid, nitrogen oxides and sulfuric acid. The washing solution discharged in the extraction generally has a total content of acid of 20 to 40 wt % based on the total weight of this washing solution and comprises for example nitric acid, nitrogen oxides, such as nitrous acid, and sulfuric acid.

The thus remaining mixture comprising the desired nitro compound is treated in at least one further extraction step for example in a second washing step with a second washing acid. In this extraction step the discharged washing solution generally has a pH of ≤4. A mixture comprising the desired nitro compound which may in principle be free from nitric acid, sulfuric acid and nitrogen oxides is typically obtained.

The thus obtained purified nitro compound may generally be used for hydrogenation to the corresponding amine.

The nitro compound obtained from the above-recited purification process or the nitro compound used for hydrogenation generally has a residual acid content of ≤300 ppm, such as sulfuric acid for example, and a pH of 2 to 4. The nitro compound, for example dinitrotoluene, generally comprises ≤800 ppm of nitrocresols or nitrophenols or mixtures thereof, ≤600 ppm of nitrobenzoic acid, for example mononitrobenzoic acid or dinitrobenzoic acid or mixtures thereof, and a residual content of ≤300 ppm, preferably ≤200 ppm and particularly preferably ≤100 ppm of nitric acid or nitrous acid or mixtures thereof, ≤50 ppm, preferably ≤10 ppm and particularly preferably ≤1 ppm of hydrocyanic acid, ≤200 ppm, preferably ≤50 ppm and particularly preferably ≤25 ppm of dinitrogen oxide, ≤400 ppm, preferably ≤200 ppm and particularly preferably ≤50 ppm of nitrogen monoxide and ≤3 ppm of sulfate.

In a preferred embodiment in addition to the nitro compound for hydrogenation the reaction mixture comprises at least one high boiler from the group consisting of nitrocresols and nitrophenols. In a particularly preferred embodiment in addition to the nitro compound for hydrogenation the reaction mixture comprises at least one high boiler from the group consisting of dinitro-cresols, trinitrocresols and nitrophenols.

In another preferred embodiment in addition to the nitro compound for hydrogenation the reaction mixture comprises no high boilers from the group consisting of nitrocresols and nitrophenols. In another particularly preferred embodiment in addition to the nitro compound for hydrogenation the reaction mixture comprises no high boilers from the group consisting of dinitro-cresols, trinitrocresols and nitrophenols.

In a further preferred embodiment in addition to the nitro compound for hydrogenation the reaction mixture comprises at least one compound from the group consisting of nitric acid, sulfuric acid, nitrogen oxides, dinitrogen monoxide, hydrocyanic acid, carbon monoxide and nitrobenzoic acid or degradation products thereof.

For the hydrogenation process according to the invention the nitro compound may be employed in pure form, as a mixture with the corresponding mono-, di- or polyamine, as a mixture with the corresponding mono-, di- or polyamine and water, as a mixture with the corresponding mono-, di- or polyamine, water and an alcoholic solvent or as a mixture with the corresponding di- or polyamine, water, an alcoholic solvent and a catalyst-reactivating addition, wherein mixtures of two or more of the abovementioned nitro compounds, of the corresponding amine compounds, of the alcoholic solvent and of the catalyst-reactivating addition may also be employed in each case.

Preferably employed catalyst-reactivating additions are aprotic solvents, in particular dimethyl-formamide (DMF) dioxane or tetrahydrofuran (THF) or a mixture of two or more thereof.

Suitable alcoholic solvents are generally lower aliphatic alcohols having 1 to 6 carbon atoms. Preference is given to using methanol, ethanol or propanol, individually or in a mixture of two or more thereof. Particular preference is given to using ethanol.

Provided that an abovedescribed mixture is employed the weight ratio of an amine compound to water is preferably in the range from 10:1 to 1:10, preferably in the range from 8:1 to 1:5 and particularly preferably in the range from 4:1 to 1:1 and the weight ratio of the amine/water mixture to at least one alcoholic solvent is preferably 1000:1 to 1:1, preferably 500:1 to 2.5:1 and particularly preferably 50:1 to 5:1.

The amount of the employed alcoholic solvent and of the catalyst-reactivating additions is not restricted in any particular way in the context of the process according to the invention and may be chosen freely as required.

The process according to the invention for hydrogenation of nitro compounds to the corresponding amines may additionally be performed in the absence of solvents. In this procedure the workup of the reaction mixture after the hydrogenation is simplified and side reactions with the solvent are moreover completely inhibited.

Salts

The purified nitro compound may generally be used for hydrogenation to the corresponding amines. However, the remaining impurities and the byproducts formed during the hydrogenation, for example high boilers, may contribute to the aging of the catalyst.

For this reason, the hydrogenation in the present process according to the invention is performed in the presence of at least one salt of the alkali metals, alkaline earth metals or of the rare earth metals.

Rare earth metals in the context of the invention are elements of the group consisting of scandium, yttrium and of the lanthanides. Lanthanides in the context of the invention are elements of the group consisting of lanthanum, cerium, praseodymium, neodymium, samarium, europium, gadolinium, terbium, dysprosium, holmium, erbium, thulium, ytterbium and lutetium.

The hydrogenation is generally performed in the presence of at least one salt of the alkali or alkaline earth or rare earth metals or mixtures thereof, preferably in the presence of at least one salt of the alkali or alkaline earth metals or mixtures thereof, preferably in the presence of at least one salt of the alkali metals or mixtures thereof, particularly preferably in the presence of at least one potassium salt or sodium salt or mixtures thereof and very particularly preferably in the presence of at least one sodium salt.

Alkali metal salts and alkaline earth metal salts and salts of the rare earths suitable in accordance with the invention preferably comprise at least one element from the group consisting of lithium, sodium, potassium, rubidium, cesium, magnesium, calcium, strontium, barium, scandium, yttrium and the lanthanides. The at least one salt preferably comprises potassium, strontium, sodium or mixtures thereof and the at least one salt particularly preferably comprises potassium, sodium or mixtures thereof.

The at least one salt of the recited alkali metals, alkaline earth metals and rare earth metals is preferably a carbonate, hydrogencarbonate, hydroxide, oxide, nitrate or carboxylate or a mixture thereof. Suitable carboxylates are for example monocarboxylates and dicarboxylates, such as acetate, formate and oxalate. Preferred salts of the process according to the invention are carbonate, hydrogencarbonate, nitrate, acetate, oxalate, formate or hydroxide or mixtures thereof, with carbonate, hydrogencarbonate, nitrate or hydroxide or mixtures thereof being particularly preferred. Cyanides and halides are generally less suitable.

It is preferable when the hydrogenation of the process according to the invention is performed in the presence of at least one salt selected from the group consisting of carbonate, hydrogencarbonate, hydroxide, oxide, nitrate or carboxylate or mixtures thereof, preferably in the presence of at least one salt selected from the group consisting of carbonate, hydrogencarbonate, nitrate or hydroxide or mixtures thereof and particularly preferably in the presence of at least one salt selected from the group consisting of hydrogen carbonate, nitrate or hydroxide or mixtures thereof.

In a first preferred embodiment the at least one salt is comprised in the catalyst. It is preferable when the at least one salt in the catalyst is present in a total concentration of 0.05 to 20 wt %, preferably 0.05 to 10 wt % and particularly preferably 0.1 to 5 wt % based on the dry weight of the catalyst.

In a second preferred embodiment the at least one salt is comprised in the liquid reaction mixture. It is preferable when the at least one salt in the liquid reaction mixture is present in a total concentration of 0.01 to 1 mol %, preferably 0.02 to 0.8 mol % and particularly preferably 0.03 to 0.6 mol % based on the supplied amount of nitro compound for hydrogenation.

Catalyst

Suitable supported catalysts for a process for continuous hydrogenation of nitro compounds to the corresponding amines in the liquid phase are generally known to one skilled in the art or are described in EP 1 678 118 B1, DE 10 2005 041 532 A1, WO 2008/138784 A1 and U.S. Pat. No. 6,140,539 for example.

Suitable active components for a catalyst for hydrogenation of nitroaromatics to the corresponding amines are generally known to one skilled in the art or are described in EP 1 678 118 B1, DE 10 2005 041 532 A1, WO 2008/138784 A1, EP 1161297 A1, EP 1165231 A1 and U.S. Pat. No. 6,140,539 for example.

The supported catalyst generally comprises at least one element from groups 7 to 12 of the periodic table of the elements as the active component. Elements from groups 7 to 12 of the periodic table of the elements suitable as the active component of the supported catalyst are for example iron, cobalt, nickel, ruthenium, rhodium, palladium, silver, osmium, iridium, platinum, gold, copper, rhenium, zinc and/or manganese.

The active component of the supported catalyst preferably comprises at least one element from groups 7 to 12 of the periodic table of the elements, particularly preferably at least one element from the group consisting of nickel, platinum, palladium, iron and cobalt, very particularly preferably at least one element from the group consisting of nickel, platinum, palladium and cobalt and especially preferably at least nickel.

The catalyst generally comprises 0 to 10 wt %, preferably 1 to 5 wt %, of noble metal based on the total weight of the catalyst.

The active component of the catalyst may optionally further comprise chromium in addition to the at least one element from the groups 7 to 12 of the periodic table of the elements.

In a preferred embodiment the supported catalyst comprises at least one salt of the alkali metals, alkaline earth metals or of the rare earth metals. It is preferable when the catalyst comprises the at least one salt in a total concentration of 0.05 to 20 wt %, preferably 0.05 to 10 wt % and particularly preferably 0.1 to 5 wt % based on the dry weight of the catalyst.

In order to suppress side reactions it is preferable to conduct the process such that the catalyst is run at its loading limit. This may be controlled through the amount of metered-in nitro compound, the amount of catalyst in the reaction mixture, the temperature or the pressure for example. The loading limit of the catalyst in the context of the invention is to be understood as meaning the amount of hydrogenatable nitrogen- and oxygen-comprising groups that can be hydrogenated by the catalyst at given pressure and temperature conditions. The nitrogen- and oxygen-comprising groups may be nitroso groups and nitrosamine groups as well as nitro groups.

In a first embodiment nickel may be used as the active component on a support as described in U.S. Pat. No. 6,140,539, wherein the catalyst is stabilized and the nickel crystallites have a bimodal nickel crystallite size distribution, a nickel content of 60 to 80 wt % based on the total mass of the catalyst and a degree of reduction of at least 70%.

Determination of the degree of reduction is generally effected during a one-hour postreduction of the stabilized catalyst at 100° C.

The two maxima of the bimodal nickel crystallite size distribution are generally at 30 to 80 Ång-ströms and 81 to 150 Ångströms. The proportion of nickel in the region of the maximum of 30 to 80 Ångströms is preferably from ≥40 to <100 wt % based on the total mass of the catalyst.

Suitable support materials for this first embodiment are for example oxides and oxide mixtures of zirconium, hafnium or silicon. The support preferably comprises $ZrO_2$, $ZrO_2.HfO_2$, $SiO_2.ZrO_2$ or $SiO_2.ZrO_2.HfO_2$ or mixtures comprising at least two of these substances. The support particularly preferably consists of these substances.

The $SiO_2$ content is preferably 0 to 20 wt % based on the total mass of the catalyst.

The $ZrO_2$ content is preferably 0 to 40 wt % based on the total mass of the catalyst.

The $HfO_2$ content is preferably 0 to 4 wt % based on the total mass of the catalyst.

Processes for producing such a catalyst are generally known to one skilled in the art or are described in U.S. Pat. No. 6,140,539 for example.

It is preferable when the active component of the supported catalyst comprises nickel in the form of nickel crystallites having a bimodal nickel crystallite size distribution and has a nickel content of 60 to 80 wt % based on the total mass of the catalyst and a degree of reduction of at least 70%.

In a second embodiment the process according to the invention for continuous hydrogenation of nitro compounds to the corresponding amines uses a supported catalyst whose active component comprises a mixture of nickel and platinum and optionally at least one additional metal, as described in EP 1678118 B1 or DE 10 2005 041 532 A1 for example.

Active components of this catalyst are generally applied to the support material in the form of mixtures. Suitable mixtures comprise nickel and platinum in an atom ratio of nickel to platinum of preferably between 30:70 and 70:30, by preference between 40:60 and 60:40 and particularly preferably between 45:55 and 55:45. Mixtures of nickel and platinum having a different atom ratio are likewise usable but often result in low product yields.

It is preferable when at least one additional metal is added to the mixture comprising nickel and platinum. Metals suitable as the additional metal are generally known to one skilled in the art or are described in DE 10 2005 041 532 A1 for example. The additional metal is preferably at least one metal from the group consisting of copper, cobalt, iron, zinc, manganese and chromium, particularly preferably at least one metal from the group consisting of copper, cobalt, iron and zinc.

The metal particles are generally polycrystalline. The characterization thereof is generally known to one skilled in the art or is described in DE 10 2005 041 532 A1 for example.

The constitution of, and processes for the characterization of, the supported catalyst whose active material may be a mixture of nickel and platinum and optionally at least one additional metal are generally known to one skilled in the art or are described in EP 1678118 B1 or DE 10 2005 041 532 A1.

The hydrogenation catalyst based on nickel and platinum and at least one additional metal and used in the process according to the invention generally comprises
1 to 5 wt % of platinum,
0.3 to 1.5 wt % of nickel,
0.05 to 1.5 wt % of the at least one additional metal and
94.65 to 97.45 wt % of support material,
each based on the total weight of the catalyst, wherein the sum amounts to 100 wt %.

The hydrogenation catalyst based on nickel and platinum and at least one additional metal and used in the process according to the invention is particularly preferably composed of
1 to 5 wt % of platinum,
0.3 to 1.5 wt % of nickel,
0.05 to 1.5 wt % of the at least one additional metal and
94.65 to 97.45 wt % of support material,
each based on the total weight of the catalyst, wherein the sum amounts to 100 wt %.

The content of non-noble metals is generally 0 to 1.6 wt %, preferably 0.1 to 0.9 wt %, based on the total weight of the catalyst.

The materials suitable as supports for the catalysts of this second embodiment are generally known to one skilled in the art or are described in EP 1678118 B1 or DE 10 2005 041 532 A1 for example. Activated carbon, carbon black, graphite or metal oxides, preferably hydrothermally stable metal oxides, for example $ZrO_2$ and/or $TiO_2$, or oxides of aluminum, such as $Al_2O_3$, or of silicon or other materials are generally employed.

It is preferable when graphite is used as the support, HSAG (high surface area graphite) having a surface area of 50 to 300 $m^2/g$ being particularly preferable in this case.

It is particularly preferable to use activated carbon as the support. A very particularly preferred embodiment is the use of physically or chemically activated carbon or carbon blacks, such as acetylene black, as the support.

Processes for producing the supported catalyst whose active material is a mixture of nickel and platinum and optionally at least one additional metal are generally known to one skilled in the art or are described in EP 1678118 B1 or DE 10 2005 041 532 A1.

The catalyst based on a mixture of nickel and platinum and optionally at least one additional metal and used in the process according to the invention is preferably employed in an amount of 0.01 to 10 wt %, preferably 0.1 to 5 wt % and particularly preferably 0.2 to 2 wt % based on the total weight of the reaction mixture.

The active component of the supported catalyst preferably comprises a mixture of nickel and platinum and optionally at least one additional metal.

The additional metal is preferably at least one metal from the group consisting of copper, cobalt, iron, zinc, manganese and chromium, particularly preferably at least one metal from the group consisting of copper, cobalt, iron and zinc.

In a third embodiment of the process according to the invention catalysts may be employed which comprise as the active component a mixture of nickel, palladium and an additional element selected from the group consisting of cobalt, iron, vanadium, manganese, chromium, platinum, iridium, gold, bismuth, molybdenum, selenium, tellurium, tin and antimony on a support. This process may in particular be used for producing tolylenediamine by hydrogenation of dinitrotoluene. The performance of a hydrogenation of nitro compounds to the corresponding amines using this catalyst is generally known to one skilled in the art or is described in WO 2008/138784 A1 for example.

The additional element is preferably selected from the group consisting of cobalt, iron, vanadium, bismuth and tin.

As the support for the catalyst of this third embodiment the materials known and customary therefor may generally be employed. It is preferable to employ activated carbon, carbon black, graphite or metal oxides, preferably hydrothermally stable metal oxides such as $ZrO_2$, $TiO_2$, $Al_2O_3$. Preferred graphites are HSAG (high surface area graphites) having a surface area of 50 to 300 $m^2/g$. Particular preference is given to activated carbons, in particular physically or chemically activated carbons, or carbon blacks, such as acetylene black.

In a further embodiment of the process according to the invention the active component of the catalyst is not Raney nickel.

The catalyst used in the process according to the invention is generally employed in an amount of 0.01 to 10 wt %, preferably 0.1 to 5 wt % and particularly preferably 0.2 to 2 wt % based on the total weight of the reaction mixture.

The catalyst is typically introduced into the reactor in a reduced and passivated state. The reduced and passivated state in the context of the invention is to be understood as meaning that the catalyst is activated after production but that the active centers are then passivated for safe-ty reasons for example by passing oxygen or carbon dioxide over them. The installation and stabilization of the catalyst under an inert atmosphere or in a non-highly-flammable solvent, for example in water or a mixture of toluenediamine and water or higher alcohols, for example butanol or ethylene glycol, are also suitable.

The invention further provides a supported catalyst for continuous hydrogenation of a nitro compound to the corresponding amine in a liquid reaction mixture comprising the nitro compound which comprises as the active component at least one element from groups 7 to 12 of the periodic table of the elements and additionally comprises at least one salt of the alkali metals, alkaline earth metals or of the rare earth metals.

Procedure

The reactors and modes of reactor operation suitable for the process according to the invention are generally known to one skilled in the art or are described in DE10 2005 041 532 A1, DE 10 2008 063 308 B4, WO 2000/035852 A1 or WO 2014/108351 A1 for example.

The process parameters, such as pressure and temperature, to be used for the process according to the invention are likewise generally known to one skilled in the art or are described in DE 10 2005 041 532 A1, DE 10 2008 063 308 B4, WO 2000/035852 A1 oder WO 2014/108351 A1 for example.

Suitable reactors are for example stirred tanks or tube bundle reactors or loop reactors, such as jet loop reactors, so-called loop venturi reactors or loop reactors with internal flow reversal as described in WO 2000/035852 A1, DE10 2005 041 532 A1, DE 10 2008 063 308 B4 or WO 2014/108351 A1. It is preferable to employ a loop reactor for the process according to the invention.

The nitro compounds are generally added at a rate that is both tailored to the catalyst activity and achieves a sufficient mixing with the flow in the loop reactor, the so-called circulation stream. The catalyst activity is generally adjusted, by addition of sufficient catalyst amounts, such that the feed stream of the nitro compounds is determined by the circulation stream so that local overconcentrations of nitro compounds (for example greater than 10 000 ppm) are avoided. In the case of a reactor with flow reversal an internal circulation flow which is greater than the circulation stream may form for example through the impact of the introduced reaction mixture onto the reactor floor or through internals. If the nitro compound is fed into the internal circulation flow in this case, the feed stream of said compound is determined by the size of the internal circulation flow in order to avoid local overconcentrations for a given conversion in the internal circulation loop.

A second feed point through which additional components, for example salts, may be introduced into the process is generally located a short distance downstream of the first feed point.

The salts of the alkali metals, alkaline earth metals or of the rare earth metals may generally be introduced into the reactor at any desired location. It is preferably when said salts are not added to the nitro compounds supplied to the reactor.

The weight hourly space velocity employed in the process according to the invention is preferably 5 to 100 kg (nitro compound)/kg (catalyst)/h, by preference 10 to 50 kg (nitro compound)/kg (catalyst)/h and particularly preferably 15 to 35 kg (nitro compound)/kg (catalyst)/h.

Suitable hydrogenating gas mixtures for continuous hydrogenation of nitroaromatics to the corresponding amines are generally known to one skilled in the art or are described in EP 1678 118 B1 for example.

Hydrogenating gas mixtures that may be employed are generally gases which comprise free hydrogen and which do not comprise damaging amounts of catalyst poisons, for example carbon monoxide. Suitable hydrogenating gas mixtures are reformer offgases or mixtures of hydrogen with nitrogen and/or carbon dioxide. It is preferable when hydrogen having a low inert gas content is employed as the hydrogenating gas mixture.

The supply of the hydrogenating gas mixtures is generally effected as a function of the hydrogen consumption by the reaction by preferably keeping the pressure prevailing in the reactor apparatus constant. Continuous removal of a portion of the gas phase allows an accumulation of inert fractions in the hydrogenating gas mixture or of inert gaseous reaction products to be avoided.

In a first embodiment the process according to the invention may be performed at temperatures of 80° C. to 200° C., preferably 110° C. to 190° C., particularly preferably 150° C. to 190° C., as described in WO 2014/108351 A1 or DE 10 2008 063 308 B4. The process of this first embodiment is generally performed at pressures of 10 to 50 bar, preferably 15 to 35 bar. The heat of reaction thus formed may be utilized to obtain steam at an overpressure of at least 4 bar using heat transferors. The parameters necessary for performing this process are generally known to one skilled in the art or are described in WO 2014/108351 A1 or DE 10 2008 063 308 B4 for example.

The process according to the invention for hydrogenation of nitro compounds to amines, for example the hydrogenation of dinitrotoluene to tolylenediamine derivatives, is preferably performed in a vertically elongated reactor, as described in WO 2014/108351 A1, which comprises at least one mixing chamber, wherein the mixing chamber or the mixing chambers are each connected at their lower end to a diffuser.

Heat transferors and cooling media suitable for performing this process are likewise generally known to one skilled in the art or are described in WO 2014/108351 A1 or DE 10 2008 063 308 B4 for example.

In a second embodiment the process according to the invention may be performed at temperatures of preferably 80° C. to 250° C., by preference 100° C. to 200° C. and particularly preferably 120° C. to 150° C. as described in WO 00/35852 A1 or DE 10 2005 041 532 A1. The process in this second embodiment is generally performed at pressures of preferably 5 to 100 bar, by preference 10 to 40 bar and particularly preferably 20 to 25 bar.

Suitable reactors are generally known to one skilled in the art or are described in WO 00/35852 A1 or DE 10 2005 041 532 A1 for example. Stirred tanks or loop reactors, such as jet loop reactors, so-called loop venturi reactors or loop reactors with internal flow reversal may generally be employed.

The amines formed in the hydrogenation may generally be withdrawn from the process continuously or discontinuously. It is preferable when the amines formed in the hydrogenation are continuously withdrawn from the process.

The withdrawal of the amines formed in the hydrogenation may be effected at any desired location. It is preferable when the withdrawal is effected from the external circulation flow upstream of the introduction of the nitro compound. Since under the recited conditions in the internal circulation flow the hydrogenation of the nitro compound is generally practically quantitative, the external circulation flow upstream of the introduction of the nitro compound comprises essentially the corresponding pure amine, water, optionally solvent and catalyst. The amine is generally removed from the withdrawn stream and sent to the purification. The catalyst and optionally water may be sent back to the external circulation flow.

The catalyst is preferably suspended in the reaction medium. The removal of the reaction product from the catalyst is generally effected by means of membrane filtration. The membrane utilized therefor may preferably be installed in the outer recirculating flow or for example in the continuously stirred tank. Alternatively the catalyst may also be retained by sedimentation in a settler installed in the outer recirculating flow or for example in the continuously stirred tank.

The membrane filtration is preferably performed at a pressure on the suspension side of 5 to 50 bar, preferably 20 to 35 bar, a pressure difference between the suspension side and the permeate side of 0.3 bar to 5 bar and a flow velocity on the suspension side of 1 to 6 m/s. Suspension side in the context of the invention is to be understood as meaning the side of the membrane filter on which the catalyst-comprising mixture is located. Permeate side in the context of the invention is to be understood as meaning the side of the membrane filter on which the catalyst-free mixture is located.

The membrane filtration may be performed continuously or discontinuously.

In continuous mode generally at least a substream of the reaction mixture is constantly run through a membrane filter. In a preferred embodiment of the process according to the invention it is preferable to arrange the membrane filter in the external circuit of a recirculating reactor.

In the discontinuous mode of the filtration the discharge reaction mixture is generally passed through a connectable purification stage consisting of at least one membrane filter and a dedicated circulation pump. In another configuration of the discontinuous filtration the reaction mixture is run through a membrane filter following the reaction.

The filter membranes employed for the process may, for example, be made of ceramic (e.g. $\alpha$-$Al_2O_3$) or stainless steel (e.g. 1.4404) and independently of the particle size of the employed catalyst preferably have a number-weighted average pore diameter in the range from 10 nm to 20 micrometers, particularly preferably in the range from 20 nm to 10 micrometers and very particularly preferably from 50 nm to 1 micrometer.

Suitable embodiments of a membrane filtration, in particular cross-flow filtration, are known to one skilled in the art and are described for example in WO2010/125025 or WO 2003/066571.

After removal of the catalyst the amines formed are generally subjected to further purification. Processes for purification of the amines produced in accordance with the invention are generally known to one skilled in the art or are described in WO 2000/035852 A1 for example. Suitable processes for purification of the amines formed are for example distillation or extraction.

DESCRIPTION OF THE FIGURES

In FIG. 1 to FIG. 4 and FIG. 7 the x-axis of the diagram shows the running time of the reaction in hours, during which DNT is metered in. In FIGS. 1, 2, 5, 6 and 7 the right-hand y-axis shows the yield of low- or high-boiling components in area % and the cometering flow in centiliters/hour. In FIGS. 3 and 4 the right-hand y-axis shows the calculated cation concentration (ideal backmixing and solubility/continuous proportional discharge) in mmol/kg. The cation concentrations are calculated for complete backmixing and continuous discharge.

FIG. 1 shows the TDA, low boiler and high boiler yields with metered addition of an aqueous solution comprising 4000 ppm of potassium bicarbonate (resulting in a concentration of 552 ppm of potassium bicarbonate).

In the curves, the data points are as follows: ♦: yield of TDA, □: yield of low-boiling components, Δ: yield of high-boiling components and ○: cometering flow of $KHCO_3$.

The vertical dashed line marks an interruption in the DNT supply for a period of almost 70 h during which the circulation stream and all other conditions are maintained.

Figure 2:
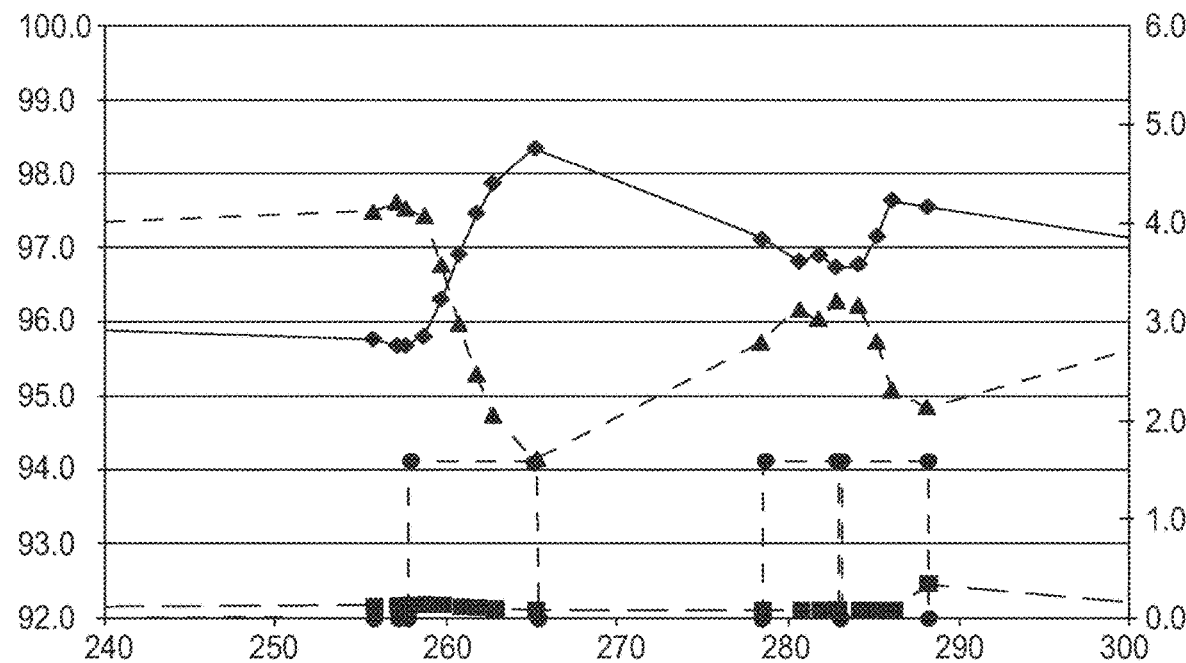

FIG. 2 shows the TDA, low boiler and high boiler yields with metered addition of aqueous solutions of potassium bicarbonate, ammonium bicarbonate and potassium hydroxide.

In the curves, the data points are as follows: ♦: yield of TDA, □: yield of low-boiling components, Δ: yield of high-boiling components and ○: cometering stream. The cometering stream consists successively of 4000 ppm of potassium bicarbonate (1), 3150 ppm of ammonium bicarbonate (2) and 2250 ppm of potassium hydroxide (3) (all aqueous solutions).

Figure 3:
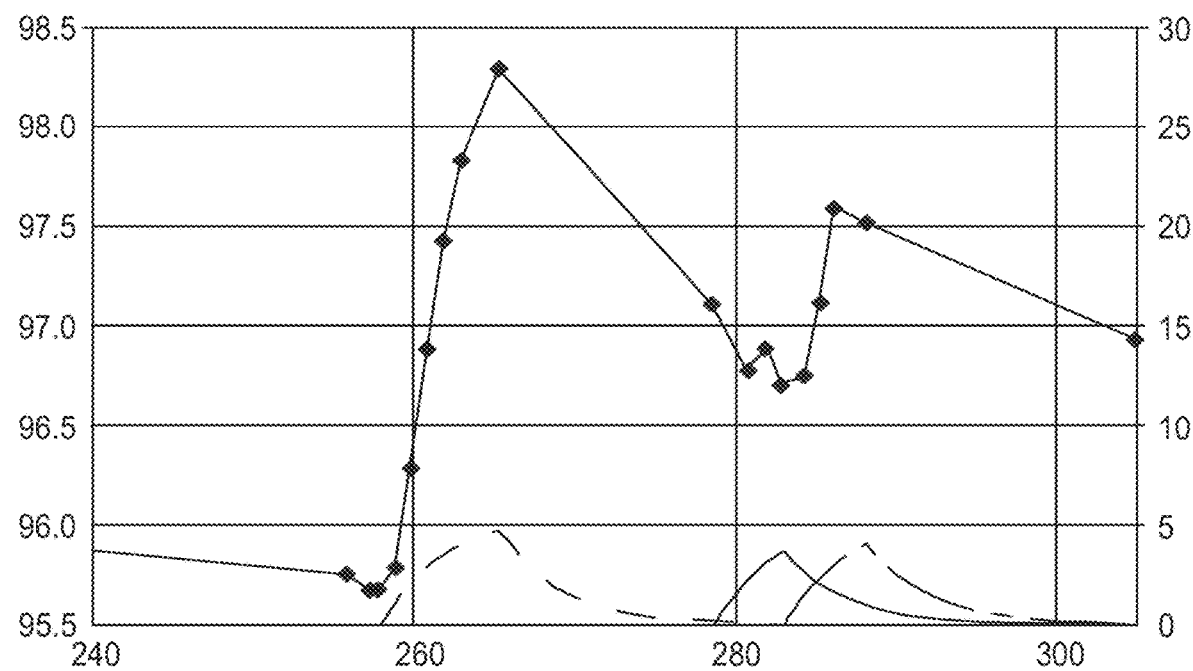

FIG. 3 shows the TDA yield with metered addition of aqueous solutions of various salts.

The data points ♦ denote the yield of TDA. The dashed curve (left-hand side) shows the calculated potassium concentration based on potassium bicarbonate (end concentration 552 weight ppm (wppm)), the solid curve (center)

shows the calculated ammonium concentration based on ammonium bicarbonate (end concentration 434 wppm) and the dotted line (right-hand side) shows the calculated potassium concentration based on potassium hydroxide (end concentration 310 wppm) in the reactor stream.

Figure 4:
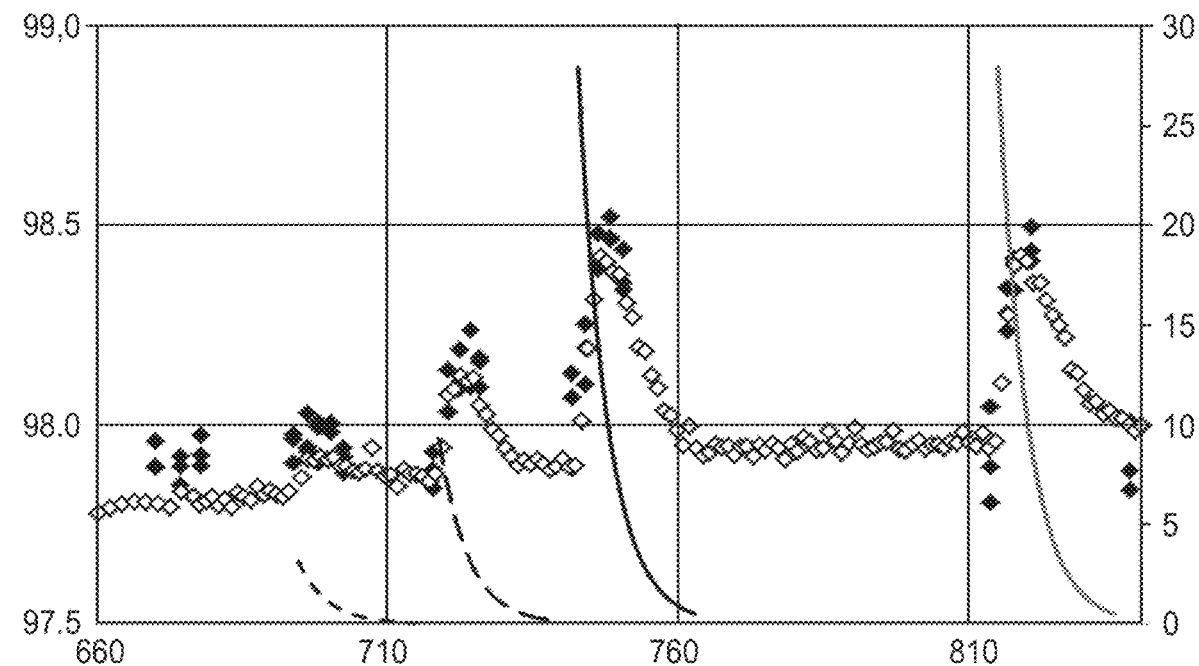

FIG. 4 shows the TDA yield with pulsed metered addition of aqueous solutions of various salts.

Data sets marked with a ◆ show the yield of TDA in area % based on the total area of all peaks in the GC. Data values marked with a ◇ show the yield of TDA in area % based on the total area of all peaks as determined in an integrated online GC.

The cation concentration, i.e. potassium concentration or sodium concentration, curves result from (from left to right) a start concentration of 121 wppm of potassium bicarbonate (dashed, short dashes), a start concentration of 363 wppm of potassium bicarbonate (dashed, long dashes), a start concentration of 1089 wppm of potassium bicarbonate (solid, black) and a start concentration of 642 wppm of sodium bicarbonate (solid, gray) in the reactor stream.

The cation concentrations are calculated for complete backmixing and continuous discharge.

Figure 5:
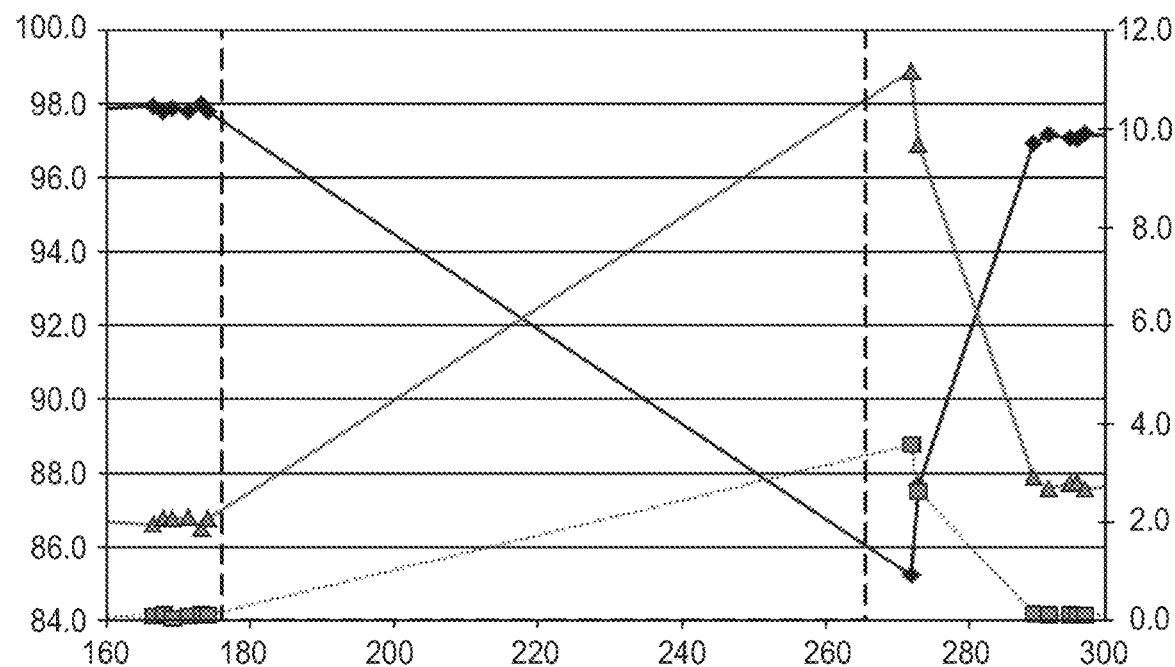
In FIG. 5 to FIG. 6 the x-axis of the diagram shows the running time of the experiment in hours since the first DNT metered addition (including interruptions to the reaction). The left-hand y-axis shows the TDA yield in area % based on the total area of all peaks in the gas chromatography (GC).

FIG. 5 shows the TDA, low boiler and high boiler yields with interruption of DNT metering in the absence of potassium bicarbonate Data points characterized as follows: ◆ represent the yield of TDA, □ show the yield of low-boiling components and Δ represent the yield of high-boiling components.

The vertical dashed lines mark an interruption in the DNT supply for a period of 90 h during which the circulation stream and all other conditions are maintained.

Figure 6:
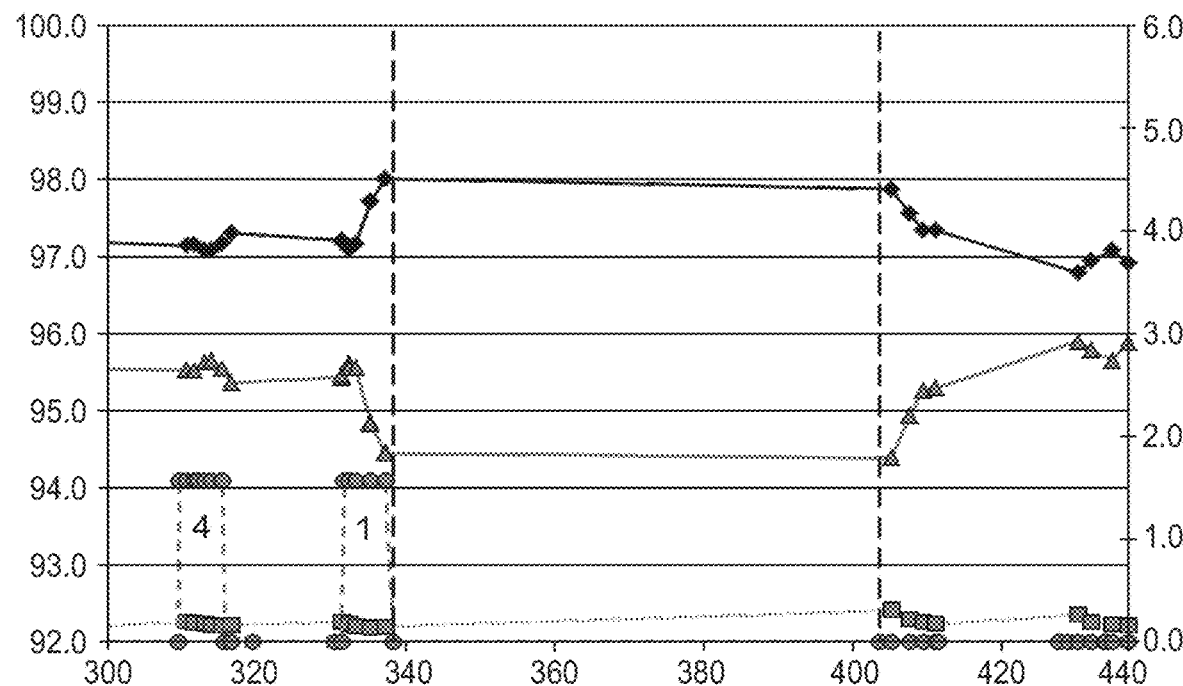

FIG. 6 shows the TDA, low boiler and high boilier yields with interruption of DNT metering in the presence of potassium bicarbonate (metered addition before interruption).

In the curves, the data points are as follows: ◆: yield of TDA, □: yield of low-boiling components, Δ: yield of high-boiling components and ○: cometering stream. The cometering stream consists successively of $H_2O$ (4) and 4000 ppm of aqueous potassium bicarbonate solution (1). The vertical dashed lines mark an interruption in the DNT supply for a period of almost 70 h during which the circulation stream and all other conditions are maintained.

Figure 7:
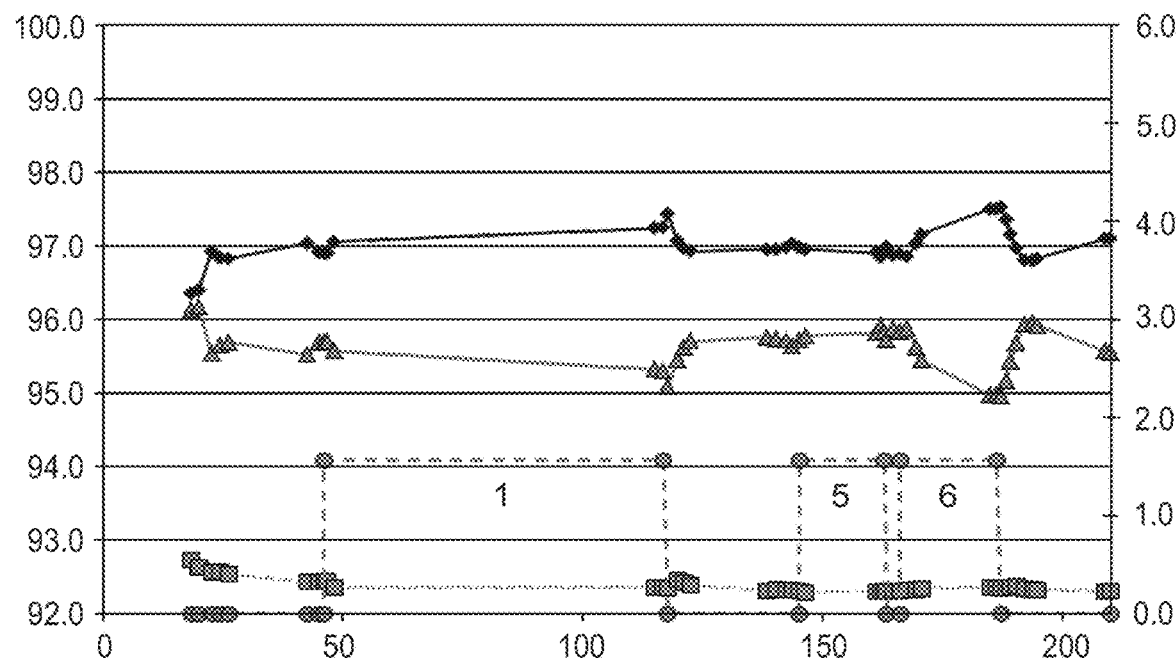

FIG. 7 shows the TDA yields, low boiler yields and high boiler yields with metered addition of aqueous solutions of potassium bicarbonate and strontium nitrate.

In the curves, the data points are as follows: ◆: yield of TDA, □: yield of low-boiling components, Δ: yield of high-boiling components and ○: cometering stream. The cometering stream consists successively of 4000 ppm of potassium bicarbonate (1) (end concentration 5.5 mmol(K)/kg), 1600 ppm of strontium nitrate (5) (end concentration 1.0 mmol(Sr)/kg) and 10 000 ppm of strontium nitrate (6) (end concentration 6.5 mmol(Sr)/kg) (all aqueous solutions).

Figure 8:
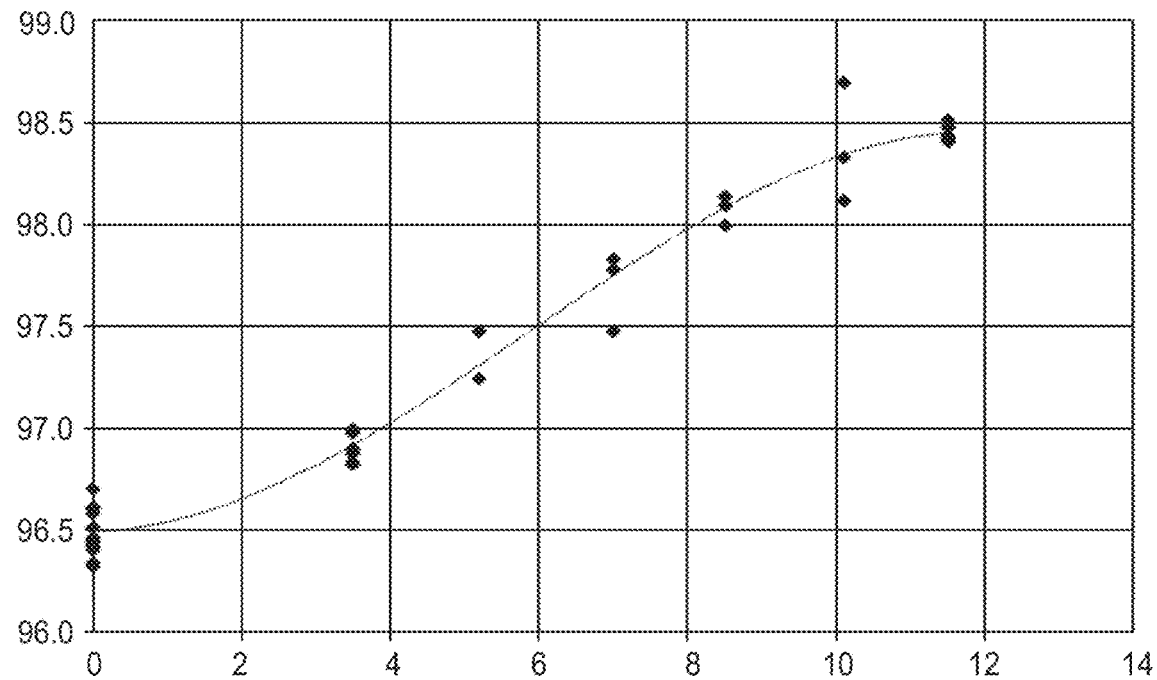

FIG. 8 shows the TDA yield with metered addition of increasing potassium concentrations.

The x-axis of the diagram shows the potassium concentration in the reactor in mmol/kg. The y-axis shows the TDA yield in area % based on the total area of all peaks in the GC.

The data points ◆ denote the yield of TDA. Said points form the basis for the trend curve in the form of a 3rd order polynomial which was determined by the least-squares method (dotted line).

Figure 9:
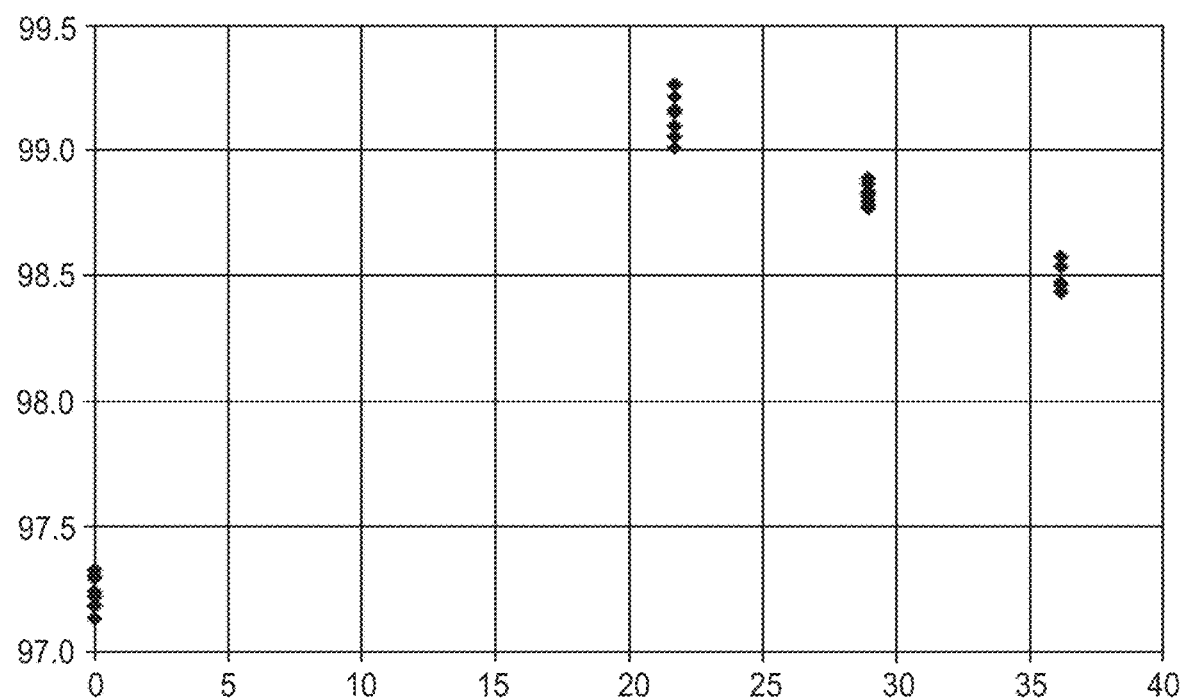

FIG. 9 shows the TDA yield with metered addition of increasing potassium concentrations.

The x-axis of the diagram shows the potassium concentration in the reactor in mmol/kg. The y-axis shows the TDA yield in area % based on the total area of all peaks in the GC.

The data points ◆ denote the yield of TDA.

EXAMPLES

The following experiments are performed in a laboratory reactor setup. This consists of a loop reactor setup which is predominantly configured as a tubular reactor but also has a stirred tank integrated in it. In the tubular reactor part of the loop reactor dinitrotoluene (DNT) and hydrogen are injected/metered into the circulation stream consisting of product and suspended catalyst (3% Pt-1% Ni/C catalyst) and mixed therewith. Installed a short distance downstream of this feed point is a second feed point through which cometerings may be supplied to the circulation stream. The hydrogen metering is effected under pressure control so that sufficient hydrogen is always available at constant pressure. Excess product leaves the loop reactor setup through a catalyst-retaining stainless steel frit installed in the stirred tank. The filtered product is then separated into a gas phase and a liquid phase in a phase separator and the gas flow set to 10 NI/h to ensure a continuous gas discharge and prevent accumulation of inert gases. In daytime operation the liquid phase is regularly withdrawn and analyzed by gas chromatography (GC with an RTX-5 amine column; injection temperature 260° C.).

Example 1

Cometering Test

Figure 1:
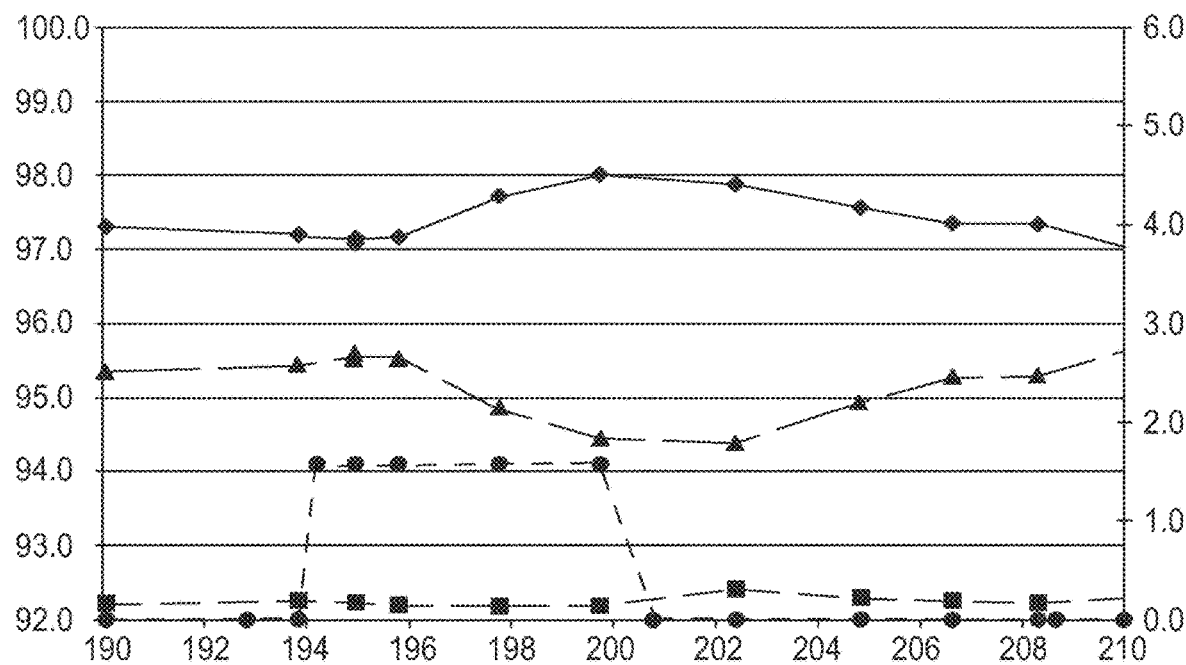

The laboratory reactor setup is charged with 3 g (dry weight) of catalyst suspended in water and operated at 185° C., 27 bar, with a circulation stream of 36 kg/h and a DNT metering rate of 100 g/h. This results in a WHSV of 33.3 kg(DNT)/kg(cat)/h. As is apparent from FIG. 1, the TDA yield gradually improves by approximately 1% during the metered addition of $KHCO_3$ solution to the reaction.

This effect gradually decreases immediately after termination of the metered addition because the salt is flushed from the reactor system with the product. The dashed line marks an interruption in the DNT supply for a period of almost 70 h during which the circulation stream and all other conditions are maintained.

Example 2

Cometering Test

The laboratory reactor setup is operated as previously except that it is charged with 5 g (dry weight) of catalyst so that the WHSV is 20 kg(DNT)/kg(cat)/h.

After a running in period of 250 h and a pronounced catalyst aging potassium bicarbonate is added and the TDA yield gradually increases by 2% (see FIG. 2). After shutdown of the metering the TDA yield gradually decreases again. Subsequent addition of ammonium bicarbonate has no effect on the TDA yield but the addition of potassium hydroxide that follows results in a gradual TDA yield increase. The increase in the TDA yield can therefore be attributed to the presence of potassium cations. Since the reaction is performed in the product and this is already strongly alkaline in nature (>60% TDA in water) it is possible to exclude an effect of the potassium on the pH as the cause.

FIG. 3 shows the calculated concentrations of the cations together with the TDA yield. As a result of the continuous addition and the backmixing of the system the salt concentrations in the circulation stream slowly and gradually increase and equally gradually decrease after termination of the metered addition. The reflection of this increase and decrease in the TDA yield is readily apparent.

Saturation concentrations of the salts in mmol/kg are calculated based on the concentration of pure DNT (5.49 mol/kg), i.e. 5.5 mmol/kg correspond to 0.1 wt % based on the reactant and also approximately describe the weight fraction in the product (neglecting $H_2$ uptake).

Example 3

Cometering Test

The following experiment is performed in a Miniplant test plant. This consists of a loop reactor set up which in one part (5.6 L) has an internal circulation flow powered by a motive jet (circulation stream consisting of product and catalyst) and in another part is configured as a tubular reactor (4.4 L). The overall set up is thermostated with thermal oil to remove generated heat. DNT is mixed in close to the motive jet and hydrogen is metered into the gas space above the internal circulation flow under pressure control. Product formed is withdrawn through a catalyst-retaining membrane so that the liquid level in the reactor part with the internal circulation flow remains constant. This discharge is regularly analyzed by GC. A fixed amount of gas is discharged above the gas space to prevent unlimited accumulation of gaseous products or impurities.

The reactor is charged with 112 g (dry weight) of 3% Pt-1% Ni/C catalyst suspended in water and operated at 185° C., 25 bar overpressure, with a circulation stream of 500 kg/h and a DNT metering rate of 2 kg/h. This results in a WHSV of 17.9 kg(DNT)/kg(cat)/h.

As is apparent from FIG. 4 the TDA yield is improved by up to 0.7% by pulsed metering of potassium bicarbonate in the highest concentration. This effect gradually decreases rapidly because the salt is continuously discharged with the product. The pulsed addition is effected by addition of a volume of 0.1/0.2 L of aqueous salt solution into the reactor. To this end, after shutoff of the DNT metered addition the liquid level in the reactor is lowered and the volume introduced into the reactor circuit with overpressure by opening a valve. The DNT metered addition is subsequently resumed and the liquid level is again set to the old value.

The concentrations are calculated based on the total reactor volume. Concentrations of the salts in mmol/kg are calculated based on the concentration of pure DNT (5.49 mol/kg), i.e. 27.5 mmol/kg correspond to 0.5 wt % based on the reactant and also approximately describe the weight fraction in the product (neglecting $H_2$ uptake). Required steady-state concentrations are in the range of examples 1 and 2.

Example 4

Potassium cometering effect during interruption of DNT addition
(=hot standby/extremely lengthy residence time of up to several days)

Interruption of the DNT addition while maintaining the other reaction conditions normally results in a severe reduction in the TDA yield through formation of high boilers. This state corresponds to an extension of the residence time and the catalyst is therefore unutilized in terms of the hydrogenation of nitro groups after reaction of the remaining DNT.

FIG. 5 shows the determined TDA yields. Over the duration of the interruption in the DNT addition the TDA content of the organic product (i.e. the TDA yield) is reduced by 13% and gradually increases after resumption of the DNT addition not to the original TDA yield value but rather to a value that is 1% lower.

FIG. 6 shows the TDA yield before and after an interruption in the DNT addition in the presence of potassium bicarbonate (metered addition before interruption). A discernible high boiler formation is not observed in this case and the TDA yield is likewise stable. The falling TDA yield after resumption of the DNT metered addition is attributable to the flushing-out of the remaining potassium bicarbonate.

Example 5

The cometering test from example 5 is performed analogously to the cometering test from example 2. The cometering stream consists successively of 4000 ppm of potassium bicarbonate (1) (end concentration 5.5 mmol(K)/kg), 1600 ppm of strontium nitrate (5) (end concentration 1.0 mmol (Sr)/kg) and 10 000 ppm of strontium nitrate (6) (end concentration 6.5 mmol(Sr)/kg) (all aqueous solutions).

Example 6

The following experiment is performed in a Miniplant test plant. This consists of a loop reactor set up which in one part (5.6 L) has an internal circulation flow powered by a motive jet (circulation stream consisting of product and catalyst) and in another part is configured as a tubular reactor (4.4 L). The overall set up is thermostated with thermal oil to remove generated heat. DNT is mixed in close to the motive jet and hydrogen is metered into the gas space above the internal circulation flow under pressure control. Product formed is withdrawn through a catalyst-retaining membrane so that the liquid level in the reactor part with the internal circulation flow remains constant. A fixed amount of gas is discharged above the gas space to prevent unlimited accumulation of gaseous products or impurities.

The reactor is charged with 112 g (dry weight) of 3% Pt-1% Ni/C catalyst suspended in water and operated at 185° C., 25 bar overpressure, with a circulation stream of 500 kg/h and a DNT metering rate of 4 kg/h. This results in a WHSV of 35.8 kg(DNT)/kg(cat)/h.

The addition of potassium carbonate is effected by supplying a continuous volume flow of a 1% aqueous salt solution into the reactor. The introduction is effected through a tube fed through at the reactor top. The solution drips into the internal circulation flow of the reactor at the edge of the push-in tube, i.e. at a point removed from the DNT feed point. Various potassium concentrations are established by variation of the volume flow of the salt solution. Once a steady-state has been established a plurality of samples are taken and analyzed by GC.

FIG. 8 plots the resulting TDA yields against the resulting steady-state potassium concentration. It is readily apparent that there is an optimum addition in terms of the improvement in the TDA yield which in this case is at about 10 mmol(K)/kg. This corresponds to 0.19 mol % of potassium based on the supplied DNT.

Example 7

The following experiment is performed analogously to example 6 except that the DNT metering rate is 2 kg/h (WHSV of 17.9 kg(DNT)/kg(cat)/h) and a 4% aqueous potassium carbonate solution is employed.

Analogously to FIG. 8, FIG. 9 plots the resulting TDA yields against the resulting steady-state potassium concentration. Once an optimum addition of the salt solution in terms of the improvement in the TDA yield has been achieved it is readily apparent that a further increase in the potassium concentration results in a deterioration of the TDA yield. The optimum addition in terms of the improvement in the TDA yield for this mode of operation is about 22 mmol(K)/kg. This corresponds to 0.36 mol % of potassium based on the supplied DNT. A further increase to about 28 mmol(K)/kg (corresponds to about 0.5 mol % of potassium based on the supplied DNT) already results in a marked deterioration in selectivity of about 0.4% in the TDA yield.

The invention claimed is:

1. A process for continuous hydrogenation of dinitrotoluene to toluenediamine in a liquid reaction mixture, the process comprising hydrogenating dinitrotoluene in the presence of a supported catalyst that comprises an active component comprising a mixture of nickel and platinum in an atomic ratio of from 30:70 to 70:30 and optionally one or more additional metals, wherein the hydrogenating is performed in the presence of at least one salt selected from the group consisting of a salt of an alkali metal, a salt of an alkaline earth metal and a salt of a rare earth metal.

2. The process of claim 1, wherein the active component of the supported catalyst comprises chromium.

3. The process of claim 1, wherein the active component of the supported catalyst comprises nickel in the form of nickel crystallites having a bimodal nickel crystallite size distribution and has a nickel content of 60 to 80 wt % based on a total mass of the supported catalyst and a degree of reduction of at least 70%.

4. The process of claim 1, wherein the supported catalyst comprises
   1 to 5 wt % of platinum,
   0.3 to 1.5 wt % of nickel,
   0.05 to 1.5 wt % of the at least one additional metal and
   94.65 to 97.45 wt % of a support material,
   based on a total weight of the supported catalyst, wherein the sum amounts to 100%.

5. The process of claim 1, wherein the at least one salt is comprised by the supported catalyst.

6. The process of claim 4, wherein the at least one additional metal is at least one metal selected from the group consisting of copper, cobalt, iron, zinc, manganese and chromium.

7. The process of claim 5, wherein the at least one salt comprised by the supported catalyst is present in a total concentration of 0.05 to 20 wt %, based on a dry weight of the supported catalyst.

8. The process of claim 1, wherein the at least one salt is comprised by the liquid reaction mixture.

9. The process of claim 8, wherein the at least one salt comprised by the liquid reaction mixture is present in a total concentration of 0.01 to 1 mol %, based on a supplied amount of dinitrotoluene for hydrogenation.

10. The process of claim 1, wherein the at least one salt comprises potassium, strontium, sodium or a mixture thereof.

11. The process of claim 1, wherein the at least one salt is a carbonate, a hydrogencarbonate, a hydroxide, an oxide, a nitrate, a carboxylate or a mixture thereof.

12. The process of claim 1, wherein the liquid reaction mixture further comprises at least one high boiler selected from the group consisting of a dinitrocresol, a trinitrocresol and a nitrophenol.

13. The process of claim 1, wherein the liquid reaction mixture comprises no high boilers selected from the group consisting of a dinitrocresol, a trinitrocresol and a nitrophenol.

14. The process of claim 1, wherein the liquid reaction mixture further comprises:
   at least one compound from the group consisting of nitric acid, sulfuric acid, a nitrogen oxide, dinitrogen monoxide, hydrocyanic acid, carbon monoxide and nitrobenzoic acid; and/or
   a degradation product of the least one compound.

15. The process of claim 1, wherein the hydrogenating is performed at a temperature of 80° C. to 250° C.

16. The process of claim 1, wherein the hydrogenating is performed in the absence of a solvent.

* * * * *

UNITED STATES PATENT AND TRADEMARK OFFICE
CERTIFICATE OF CORRECTION

PATENT NO. : 10,538,478 B2
APPLICATION NO. : 16/340593
DATED : January 21, 2020
INVENTOR(S) : Armin Lange de Oliveira et al.

It is certified that error appears in the above-identified patent and that said Letters Patent is hereby corrected as shown below:

On the Title Page

On page 2, in Column 1, item (56), Other Publications, Lines 1-2, delete "Hadrogenation" and insert -- Hydrogenation --, therefor.

In the Specification

In Column 2, Line 47, delete "in-completely." and insert -- incompletely. --, therefor.

In Column 2, Line 49, delete "corn-pounds" and insert -- compounds --, therefor

In Column 3, Line 53, delete "corn-pounds" and insert -- compounds --, therefor.

In Column 5, Line 27, delete "trini-trophenol." and insert -- trinitrophenol. --, therefor.

In Column 6, Line 26, delete "dinitro-cresols," and insert -- dinitrocresols, --, therefor.

In Column 6, Line 34, delete "dinitro-cresols," and insert -- dinitrocresols, --, therefor.

In Column 6, Line 55, delete "dimethyl-formamide" and insert -- dimethylformamide --, therefor.

In Column 6, Line 63, delete "abovedescribed" and insert -- above described --, therefor.

In Column 8, Lines 1-2, delete "hydrogen carbonate," and insert -- hydrogencarbonate, --, therefor.

In Column 9, Line 15, delete "Ång-ströms" and insert -- Ångströms --, therefor.

In Column 11, Line 30, delete "safe-ty" and insert -- safety --, therefor.

In Column 15, Line 33, delete "boilier" and insert -- boiler --, therefor.

Signed and Sealed this
Thirtieth Day of June, 2020

Andrei Iancu
*Director of the United States Patent and Trademark Office*